(12) United States Patent
Noro et al.

(10) Patent No.: US 8,906,212 B2
(45) Date of Patent: Dec. 9, 2014

(54) METHOD FOR EVALUATING CORROSION RESISTANCE OF CANS TO CONTENTS

(75) Inventors: Hisato Noro, Kanagawa (JP); Yoichiro Yamanaka, Hiroshima (JP); Junichi Kitagawa, Hiroshima (JP); Yoshihiko Yasue, Chiba (JP); Hisao Yasuhara, Chiba (JP)

(73) Assignee: JFE Steel Corporation, Tokyo (JP)

( * ) Notice: Subject to any disclaimer, the term of this patent is extended or adjusted under 35 U.S.C. 154(b) by 0 days.

(21) Appl. No.: 14/009,426

(22) PCT Filed: Apr. 10, 2012

(86) PCT No.: PCT/JP2012/060201
§ 371 (c)(1),
(2), (4) Date: Nov. 27, 2013

(87) PCT Pub. No.: WO2012/141323
PCT Pub. Date: Oct. 18, 2012

(65) Prior Publication Data
US 2014/0090987 A1 Apr. 3, 2014

(30) Foreign Application Priority Data
Apr. 12, 2011 (JP) ................................ 2011-087930

(51) Int. Cl.
*G01N 17/02* (2006.01)
(52) U.S. Cl.
CPC ..................................... *G01N 17/02* (2013.01)
USPC ........................ 204/404; 205/775.5; 205/777
(58) Field of Classification Search
USPC ................................ 204/404; 205/775.5–777
See application file for complete search history.

(56) References Cited

FOREIGN PATENT DOCUMENTS

| JP | 61-18842 | | 1/1986 |
|---|---|---|---|
| JP | H08-211006 | * | 8/1996 |
| JP | 11-014582 | | 1/1999 |
| JP | 2934164 | | 8/1999 |
| JP | 2004-333468 | | 11/2004 |
| JP | 2009-168684 | | 7/2009 |
| JP | 2010-133749 | | 6/2010 |
| JP | 2011-102790 | | 5/2011 |

OTHER PUBLICATIONS

International Search Report, PCT/JP2012/060201, Jun. 26, 2012.
Supplementary European Search Report dated Oct. 2, 2014 in corresponding European Patent Application No. 12771259.4.

* cited by examiner

*Primary Examiner* — J. Christopher Ball
(74) *Attorney, Agent, or Firm* — Young & Thompson (57) ABSTRACT

A method to evaluate the corrosion resistance of a can to a content includes filling the can with the content to form a specimen, setting the specimen in an apparatus capable of blocking an outside atmosphere from entering the specimen, optionally saturating the content with nitrogen gas to expel dissolved oxygen present in the content, thereafter while maintaining the temperature of the content at a constant temperature in the range of 25 to 60° C., applying a constant potential that is more anodic than an immersion potential by 50 mV to 200 mV to the can of the specimen, and evaluating the corrosion resistance of the can to the content based on the accumulated amount of electricity generated during a time appropriately selected from 6 to 48 hours immediately after the application of the constant potential.

4 Claims, 10 Drawing Sheets

METHOD FOR EVALUATING CORROSION RESISTANCE OF CANS TO CONTENTS

TECHNICAL FIELD

The present invention relates to a technique for quickly evaluating the corrosion resistance of cans to contents that allows for quick prediction within 48 hours of results of a long-term, usually about 2 year long, actual fill test (hereinafter, also "pack test") which manufacturers of canned products in fields such as canned foods perform in order to evaluate the corrosion resistance of cans to contents. Mainly, the invention relates to a technique for improving the efficiency in the cycles of the development of products such as coated metal sheets for the production of cans, and cans themselves.

BACKGROUND ART

Metal sheets coated with resin films or coating materials are used in the form of cans for containing items such as foods and beverages. If defects occur in the films inside the cans during storage, the metal sheets are corroded on a macroscopic scale. This corrosion can lead to serious troubles such as swelling of cans due to generated gas, leakage of contents due to perforation corrosion, and food poisoning due to deterioration of contents. Thus, the evaluation of film defects in the cans is an important issue from the viewpoint of public health and also for the manufacturers of metal sheets and canned products.

The evaluation of film defects has been exclusively based on the enamel rate value method (hereinafter, abbreviated to "ERV" method). For example, Patent Literatures 1 to 3 disclose methods for evaluating the degree of metal exposure at defective film portions in coated metal sheets by the ERV method.

Further, Patent Literature 6 discloses an evaluation method, an improved version of the ERV method, which is capable of evaluating the degree and location of the exposure of base steel in tin-plated cans without being affected by tin.

Film defects occur in the inner face of cans by the three types of causes: (1) factors during the formation of films or the production of cans, (2) impacts such as when filled cans are dropped, and (3) influences of contents during long storage. The ERV method and the method disclosed in Patent Literature 6 are effective for detecting film defects ascribed to the cause (1) which occur before the filling of contents. However, these methods cannot be used for the evaluation of defects due to the types (2) and (3) which occur after the filling of contents.

As is known from Patent Literature 4, a technique is disclosed which evaluates the tendency of the occurrence of film defects in the inner face of metal cans after the cans are filled with contents. This technique is mainly developed for beverage cans, and relates to a measurement apparatus which permits film defects occurring in the inner face of cans by impacts to be measured under conditions similar to those actually experienced by canned products. In order to realize the measurement of film defects in an environment similar to that actually experienced by filled cans, the characteristic of this apparatus lies in that it is provided with a sealing function, a deaerating function, an inner pressure control function, a temperature control function, a collision device for applying an impact load to the cans, and an electrochemical measuring device for measuring the electrical resistance of the films in a sealed environment.

A similar apparatus for evaluating coated metal sheets is disclosed in Patent Literature 5.

These apparatuses measure, in particular, the degree of film defects caused by impacts (2) in the inner face of cans by making use of the electrical resistance of films.

CITATION LIST

Patent Literature

[PTL 1] Japanese Unexamined Patent Application Publication No. 6-50926
[PTL 2] Japanese Unexamined Patent Application Publication No. 6-74930
[PTL 3] Japanese Unexamined Patent Application Publication No. 6-74941
[PTL 4] Japanese Patent No. 2934164
[PTL 5] Japanese Patent No. 2895411
[PTL 6] Japanese Patent No. 1332395

SUMMARY OF INVENTION

Technical Problem

However, an evaluation of film defects of type (3) carried out by can manufacturers using the above apparatus for as long a duration of time as about 2 years only provides results which are not so much different from those obtained by actually storing a number of filled cans in the test environment and opening the cans one after another with the lapse of time to evaluate the condition of contents.

Under the circumstances described above, manufacturers of metal sheets and canned products are obliged to spend a long time on the evaluation of corrosion resistance in content storage environments. This has been a longtime problem inhibiting the shortening of cycles in the development of products such as coated metal sheets for the production of cans, and cans themselves.

An object of the present invention is to provide an accelerated test method capable of quickly predicting evaluation results which usually take as long as about 2 years to become clear. That is, it is an object of the invention that the corrosion resistance of cans to contents obtained in a long-term storage environment is evaluated and estimated in a short time.

Solution to Problem

In order to achieve the above object, the present inventors carried out extensive studies on corrosion phenomena which take place when defects in the inner face of cans come to be in contact with contents in a storage environment.

As a result, the present inventors have obtained findings including the following.

(1) In the case of laminated cans where coated metal sheets are laminated steel sheets, ultra fine defects (pinholes) are produced in the laminated film, to a greater or less extent, during the can-body forming process. Thus, it is possible to detect the immersion potential for performing an electrochemical measurement while the cans are filled with contents.

(2) In an actual storage environment, the anodic dissolution of iron occurs from such film defects by a corrosive reaction (an electrochemical reaction).

(3) Such anodic dissolution from film defects may be accelerated by polarizing the metal at a potential that is more anodic than the immersion potential by an appropriate potential. The total amount of electricity carried by the resultant anodic current is consistent with the order in a long-term pack test in an actual storage environment.

The present invention has been completed based on the above findings and after further studies. A summary of the invention is as described below.

(1) A method for evaluating the corrosion resistance of a can to a content, the can being formed of a metal sheet and having an opening, at least an inner face or both an outer face and an inner face being coated with a resin film or a coating material, the method including filling the can with the content to form a specimen, setting the specimen in an apparatus capable of blocking an outside atmosphere from entering the specimen, while maintaining the temperature of the content at a constant temperature in the range of 25 to 60° C., applying a constant potential that is more anodic than an immersion potential by 50 mV to 200 mV to the can of the specimen, and evaluating the corrosion resistance of the can to the content based on the accumulated amount of electricity generated during a time appropriately selected from 6 to 48 hours immediately after the application of the constant potential.

(2) The method for evaluating the corrosion resistance of the can to the content described in (1), wherein the constant anodic potential is applied after the specimen is set in the apparatus capable of blocking an outside atmosphere from entering the specimen and the content is saturated with nitrogen gas to expel dissolved oxygen present in the content.

(3) A measurement apparatus for evaluating the corrosion resistance of a can to a content, the apparatus being used in the method for evaluating the corrosion resistance of a can to a content described in (1) or (2), the apparatus including:

a) an electrolytic cell lid A configured to be tightly compressed against the opening to block an outside atmosphere from entering the specimen, the electrolytic cell lid including the following i) to iv):

i) a nitrogen gas injection section, ii) a gas vent section, iii) a salt bridge for electrically contacting the content and a reference electrode D disposed outside the specimen through ionic conduction, and iv) an electrode section for setting a potential difference with respect to the can via the content;

b) a fastening means B for tightly compressing the opening to the electrolytic cell lid A;

c) a thermostat means C for heating and keeping warm the specimen;

d) the reference electrode D; and e) a potentiostat E connecting the reference electrode D, the electrode section, and the metal sheet forming the can.

Advantageous Effects of Invention

According to the present invention, the corrosion resistance of cans to contents may be evaluated as quickly as in 6 to 48 hours without entailing a 2 year long pack test usually performed by can manufacturers. Thus, improvements may be obtained in the efficiency in the cycles of developing products such as coated metal sheets at steel sheet manufacturers and cans at can manufacturers. Further, can manufacturers may use the invention as a tool for quickly evaluating the degree of corrosion resistance expected when items never canned before are packaged in existing cans.

As mentioned above, the present invention makes it possible to evaluate the order or degree of corrosion resistance of cans with respect to contents of interest based on the accumulated amount of electricity produced by anodic current, without storing the canned products for a long time. Thus, in particular, the present invention allows for effective improvement of the corrosion resistance of coated metal sheets based on the optimization of conditions for manufacturing laminated metal sheets or the selection of laminate films, as well as permits can manufacturers to effectively examine can forming methods in consideration of corrosion resistance.

DESCRIPTION OF EMBODIMENTS

The present invention will be described in detail hereinbelow.

Figure 1:
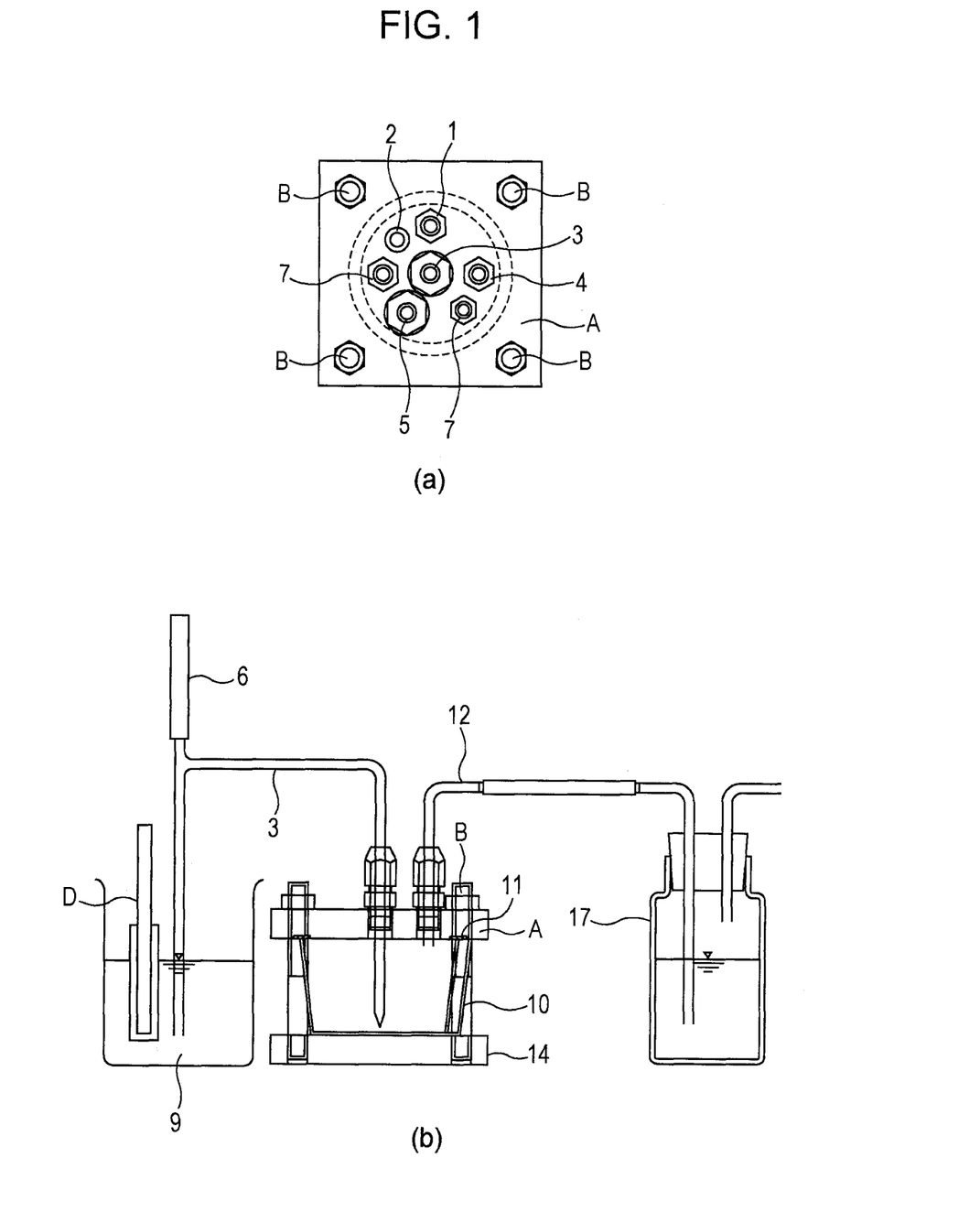
FIG. 1 is a set of schematic views illustrating a measurement apparatus for carrying out an inventive method.
Figure 2:
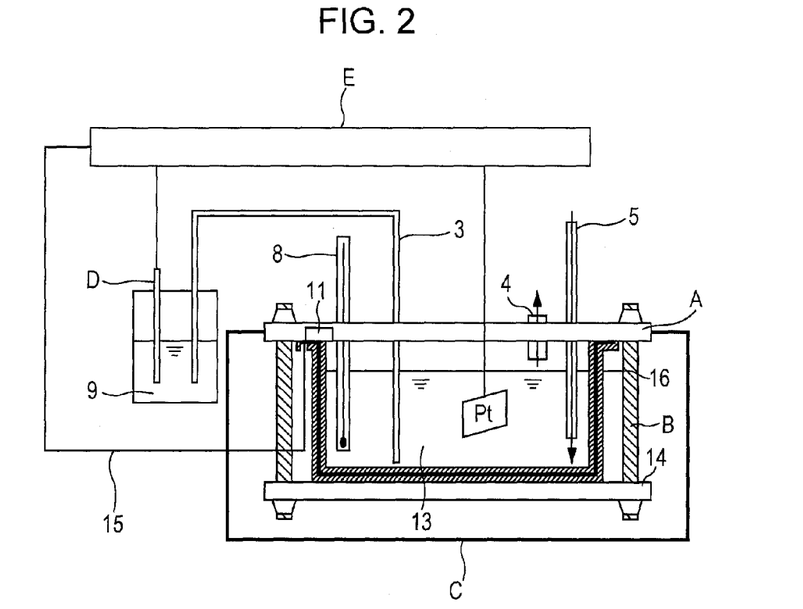
FIG. 2 is a schematic view illustrating a connection of a potentiostat to a reference electrode, a specimen and a platinum electrode in FIG. 1.

FIGS. 1 and 2 schematically illustrate a measurement apparatus according to an embodiment of the present invention. A specimen (10) consists of a can (16) and a content (13) filling the can. At least the inner face of the can is coated with a resin film or a coating material, and the can has an opening without a closure with a lid.

The measurement apparatus includes a bottom plate (14) which, in combination with an electrolytic cell lid (A) fitted with a packing (11), sandwiches the specimen (10) so as to tightly compress the opening of the can (16) of the specimen (10) against the packing (11), and a fastening means (B), for example support rods (bolts and nuts), for fastening the electrolytic cell lid (A) to the bottom plate (14). To the electrolytic cell lid (A) are fixed members such as i) a platinum electrode for setting a potential difference with respect to the can (16) of the specimen (10) via the content (13) of the specimen (10), ii) a salt bridge (3), iii) a nitrogen inlet pipe (5) and a water-sealed gas vent pipe (12) defining a nitrogen gas injection section for deaeration with nitrogen, iv) a thermometer (8) for measuring the temperature of the content (13), and v) airtight stoppers (7) to which content sampling pipes and the like can be connected.

The specimen (10), the platinum electrode and the salt bridge (3) are connected to a potentiostat (E). The can (16) of the specimen (10) and the potentiostat (E) are connected via an electrical wire that has been spot welded after the removal of an insulating film such as a coating film on the outer side of the can (16) of the specimen (10). For the content (13) of the specimen (10), the platinum electrode is immersed in the content (13), the platinum electrode being connected to the potentiostat (E). Further, a reference electrode (D) such as a KCl saturated Ag/AgCl electrode is connected to the potentiostat (E), and the reference electrode (D) and the content (13) are electrically connected to each other via the salt bridge (3). The whole of this measurement apparatus is configured to be temperature-controlled by being soaked in a thermostat means (C), for example, a water bath.

While the fastening means (B) is illustrated as being bolts and nuts, the fastening means (B) in the present invention is not limited thereto and may be, for example, a clamping tool such as a vise or a clamp. Further, the thermostat means (C) is not limited to a water bath, and may be other thermostat means such as an electromagnetic or electric heater.

In an evaluation method according to the present invention, a can (16) is filled with a content (13), then this specimen is set in an apparatus capable of blocking an outside atmosphere from entering the specimen, the immersion potential of the specimen is measured while maintaining the temperature of the content at a constant temperature in the range of 25 to 60° C., thereafter a constant potential that is more anodic than the measured immersion potential by a potential selected from 50 mV to 200 mV is applied, and the corrosion resistance is evaluated based on the accumulated amount of electricity generated during a time appropriately selected from 6 to 48 hours immediately after the application of the constant potential.

The can evaluated herein is formed of a metal sheet and has an opening, and at least an inner face or both an outer face and an inner face are coated with a resin film or a coating material.

The shape of the opening is not limited as long as the can may be tightly compressed against an electrolytic cell lid (A) via a packing (11). An edged can body as drawn which has not been subjected to edge trimming or edge seaming is desirable because such a can is easily tightly compressed to a packing. Spot welding on a can body damages a film on the inner face and can affect a corrosion behavior. Thus, the can (16) of the specimen is desirably connected to the potentiostat via an electric wire (15) that is spot welded on the outer side of the edge of the opening which does not contact with the content.

The metal sheet may be a steel sheet for canning such as a laminated steel sheet or a tin plate. The resin films and the coating materials for coating the inner face of the metal sheets are not particularly limited, and any known materials may be used. The coating methods are not particularly limited and may be conventional. Further, commercially available coated metal sheets may be utilized. Although the present invention concerns a technique for evaluating the corrosion resistance of internally coated cans with respect to contents, cans that are appropriately coated internally as well as externally may be tested.

The contents packed into the cans may be selected appropriately in accordance with the purpose of evaluation. When the purpose is to predict evaluation results of a long-term pack test performed by can manufacturers, it is desirable to use the same food as actually packaged. The configurations of the contents are not particularly limited as long as the contents are conductive, and any of solids, liquids, mixtures of solids and liquids, gels and sols may be evaluated. Here, the solids to be tested in the invention may be foods such as jelly and congealed food that contain water, are conductive and can closely fill the substantial proportion of the can by itself. That is, solid foods with markedly low conductivity such as biscuits, rice and chocolate are excluded.

After the can (16) is filled with the content (13), the specimen (10) is set in the measurement apparatus.

In the measurement apparatus, the specimen (10) is sandwiched between an electrolytic cell lid (A) fitted with a packing (11), and a bottom plate (14) and is fastened with support rods (bolts and nuts) as a fastening means B. Thus, the packing (11) can block an outside atmosphere from entering the specimen. In this state, the whole of the measurement apparatus is set in a thermostatic water bath controlled at a constant test temperature. After the temperature of the content is confirmed to have reached the test temperature, an immersion potential measurement is carried out for 30 minutes. When the immersion potential becomes stable within 10 minutes after the temperature of the content is confirmed to have reached the test temperature, the measurement may be terminated at the lapse of 10 minutes.

In the case where the evaluation is made after expelling dissolved oxygen from the content, the following operations are preferably carried out before the whole of the measurement apparatus is set in a thermostatic water bath controlled at a constant test temperature: a nitrogen inlet pipe (5) attached to the electrolytic cell lid (A) of the measurement apparatus is inserted into the content (13) and, while maintaining the insertion, nitrogen gas is injected and discharged out of the specimen through a water-sealed gas vent pipe (12) attached to the electrolytic cell lid (A). In this manner, the content is saturated with the nitrogen gas to expel dissolved oxygen present in the content. The expelling time may be selected appropriately in accordance with, for example, the volume of the specimen. In the case of a ½ lb can, the dissolved oxygen may be expelled in about 30 minutes. It is a preferred practice that after the dissolved oxygen is expelled, the nitrogen inlet pipe (5) is slid with respect to the electrolytic cell lid (A) and is lifted up from the content, thereby switching the mode to deaerate the gas phase, and the whole of the measurement apparatus is set in a thermostatic water bath controlled at a constant test temperature.

Then, a constant potential is applied to the specimen. This constant potential is more anodic by an appropriate potential than the immersion potential measured after the lapse of 10 to 30 minutes after the temperature of the content reaches the test temperature. Lastly, an accumulated amount of electricity generated during an appropriate time immediately after the application of the constant potential is calculated, and the corrosion resistance is evaluated based on the accumulated amount of electricity.

The temperature of the content (the test temperature) is an appropriate temperature that is maintained constant and is selected from the range of 25 to 60° C.

Conventional long-term pack tests are frequently performed at an actual storage temperature. It is preferable also in the present invention that the temperature of the content be selected in line with temperatures adopted in conventional long-term pack tests. Thus, the lower limit is specified to be 25° C. The upper limit is specified to be 60° C. to meet the demand that the corrosive reaction be accelerated at room temperature or an elevated temperature as well as in consideration of the glass transition temperatures of the coating films and the laminate films on the cans.

The accumulated amount of electricity generated during the given time is calculated based on the anodic current. In detail, while the above constant potential is applied to the can of the specimen, the current passing through the electric wire (15) on the can of the specimen is measured with the potentiostat shown in FIG. 2 for a time appropriately selected from 6 to 48 hours. This current is produced by the dissolution of divalent iron ions from the base steel sheet into the content. Integrating the current (=charges/time) with respect to the measurement time gives the accumulated amount of electricity generated during that period. The calculation is possible through two methods: one is to combine the amounts of current (=charges) measured per second, and the other is to obtain the average value of the measured current values and multiply the average by the measurement time in second. Both of these methods give the same result. This accumulated amount of electricity is in proportion to the absolute amount of divalent iron ions dissolved into the content.

The duration of time that is appropriately selected from 6 to 48 hours is measured from immediately after the application of the constant potential. Here, the time is selected from 6 to 48 hours for the following reasons. Stable assessment is often difficult if the time selected is less than 6 hours, and the obtained results are very likely to impair correct prediction of results of a 2 year long test. Measurements requiring more than 48 hours are difficult to serve as accelerated test methods and also raise a concern that the evaluation may be adversely affected by the content being rotten due to the contamination with bacteria depending on the timing of a retort treatment described below. After being filled and sealed, canned foods or canned beverages are usually subjected to a retort treatment in which they are placed in a retort vessel and are sterilized with high temperature steam. The treatment prevents the contents from becoming rotten in a storage environment.

If a retort treatment is performed in such a manner that the whole of the inventive measurement apparatus including the can filled with the content is placed in a retort vessel, it will become necessary that, for example, the electric wires be insulated, materials of such members as the electrolytic cell lid and the packing be redesigned, and the retort vessel be modified. Thus, the need of evaluating the effects of treatments such as retort treatment and dent treatment described later in a simple manner according to the inventive measurement method is efficiently met by sealing a filled can with a temporary lid and subjecting the canned product to the treatments before the filled can is set in the inventive measurement apparatus.

When such a simple approach is adopted, however, it is difficult to perfectly prevent any contamination with bacteria between when the temporal lid is removed after the treatment and when the can is sealed again with the electrolytic cell lid. Consequently, the evaluation of an easily rotten content for more than necessary may result in the accumulation of a decomposition gas in the salt bridge to impair the ionic conduction, thus leading to an instability of potential. Further, the evaluation with such a rotten content does not provide reliable results. According to the studies carried out by the present inventors, there is no marked influence of bacterial rot on any kinds of food contents as long as the evaluation time is not more than 48 hours. The selected duration of time is preferably 24 to 48 hours.

The constant potential applied to the specimen is a potential that is more anodic than the immersion potential by a potential selected from 50 mV to 200 mV. This range is adopted based on the results of studies described below.

Figure 3:
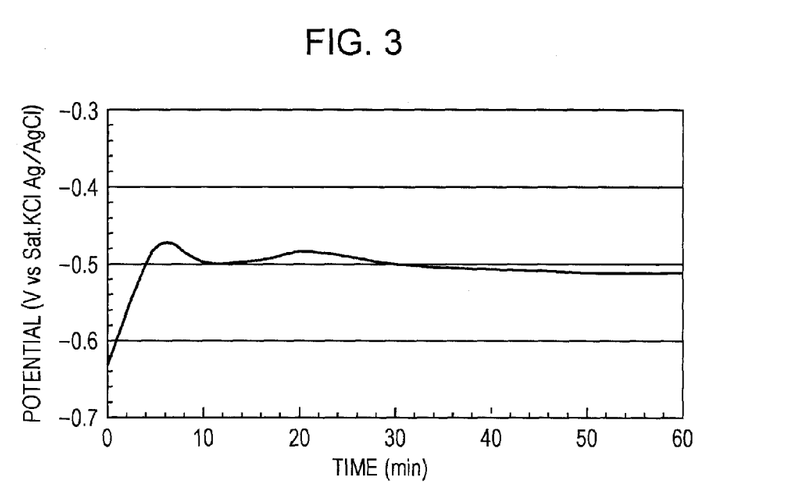
FIG. 3 illustrates an example of measurement of immersion potential with respect to a laminated can filled with a NaCl solution.

FIG. 3 illustrates an example of measurement of immersion potential with respect to a PET-laminated can filled with a 2% NaCl solution at 50° C. according to the use of the measurement apparatus illustrated in FIGS. 1 and 2. In this example, taken as the immersion potential is a stable potential after 40 minutes from the initiation of the measurement, the time at which the measured potential starts to become stable.

The reason why such a stable immersion potential is observed with cans that are formed of a laminated sheet coated with an insulating film is probably because a small number of pinholes are produced in the laminate film during the production of cans. The immersion potential is unstable for about 30 minutes after the can is filled with the 2% NaCl solution. This instability is probably because a time is necessary for the pinholes to be completely in contact with the liquid and become stabilized. Usually, the potential applied to the specimen is set after the can filled with the content is subjected to deaeration with nitrogen for about 30 minutes and thereafter a stable immersion potential is obtained. However, the omission of the deaeration with nitrogen does not affect evaluation results when the pH of the content is below 4. The reason for this is because the reaction at the cathode (in this case, the platinum electrode), which is a half reaction making a pair with the anodic reaction, namely, the dissolution of divalent iron ions from the base steel sheet, is governed by the reduction reaction by hydrogen ions present in larger amounts than dissolved oxygen.

Figure 4:
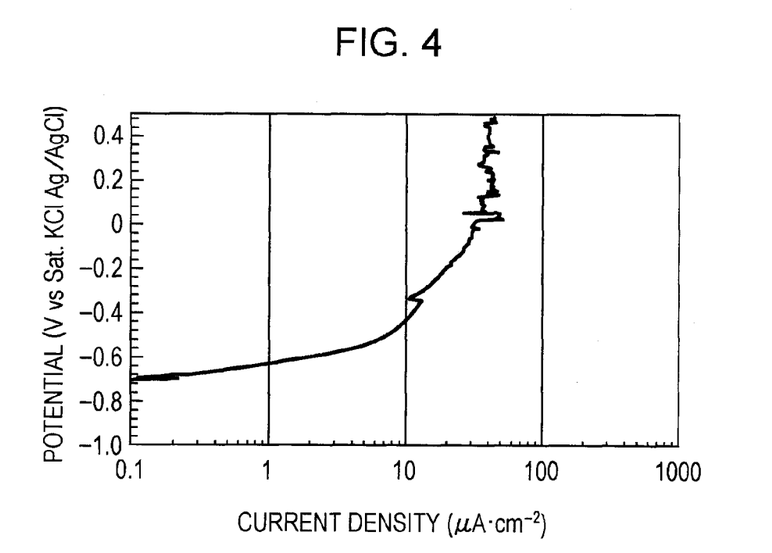
FIG. 4 illustrates an example of measurement of anodic polarization with respect to a laminated can filled with a NaCl solution.
Figure 5:
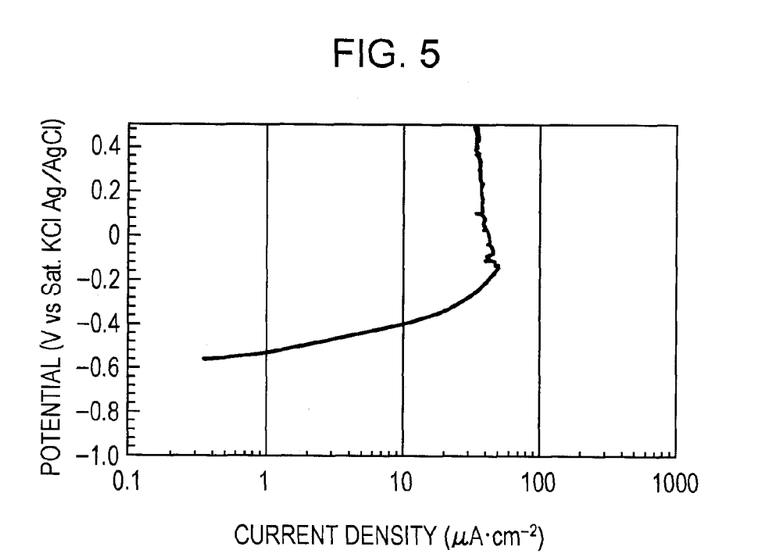
FIG. 5 illustrates an example of measurement of anodic polarization with respect to a laminated can filled with tomato ketchup.

FIGS. 4 and 5 illustrate examples of measurements in which two PET-laminated cans set in two respective apparatuses and maintained at 50° C., one filled with a 2% NaCl solution and the other with commercial ketchup, were deaerated with nitrogen for about 30 minutes and were thereafter anodically polarized at a potential sweep rate of 20 mV/min. As illustrated in these examples, while the immersion potentials of the two cans are different immediately before the polarization test, each case shows a sharp rise in anodic current when the potential is more anodic (positive) than the immersion potential by up to about 300 mV (=0.3 V). The anodic current is raised with an increase in potential. However, the rate of rise gradually decreases, and the increase in anodic current is substantially saturated after a specific potential. This saturation region probably indicates that the surface of defective or brittle portions in the inner face of the PET-laminated can has been passivated to a degree that is impossible in a usual storage environment. This passivation phenomenon that does not occur in a usual storage environment is considered, in a strict sense, to be simultaneous occurrences of the formation of the passivation film and the destruction thereof by chloride ions.

The anodic reaction in the specimen may be accelerated by applying a potential that is within a specific range below the potential which causes the substantial saturation of the increase in anodic current. This range of potentials may be determined by subjecting cans that are filled with respective contents of different kinds having markedly different corrosive properties to constant potential electrolysis at a potential below the potential at which the above saturation is reached. For example, the following results are obtained by an experiment in which commercial tomato ketchup and cut tomato in juice having at least single-digit difference in the amounts of Fe dissolved into contents according to a 1 year pack test (amounts of Fe dissolution: tomato ketchup>cut tomato in juice) are packed into PET-laminated cans, and the amounts of Fe dissolution are monitored for 48 hours with respect to the accumulated amounts of electricity while changing stepwise the magnitude of applied potential in the range of 0 to 300 mV based on the immersion potential as the reference. The application of less than 50 mV potential causes so small an amount of Fe dissolution that it is difficult to discriminate the corrosive properties of the contents within 48 hours. The application of a potential exceeding 200 my may result in a reversed order of the accumulated amounts of electricity obtained with tomato ketchup and cut tomato in juice, making it difficult to discriminate the corrosive properties of the contents. The reason why the magnitude relation between the accumulated amounts of electricity becomes unstable by the application of more than 200 mV potential is probably because such a potential region corresponds to a transition region in which part of the inner faces of the cans in contact with the contents has started to be passivated and the consequent slight difference in areas tends to become apparent as the reversed relation.

As shown in the above examples, the potential applied to a can of a specimen in order to predict results of a long-term pack test (hereinafter, "acceleration potential") is optimally more anodic than the stable immersion potential by a potential in the range of 50 mV to 200 mV. The value and polarity of the acceleration potential are very important in the prediction of results of an actual pack test. Setting the acceleration potential to a value which is more cathodic than the immersion potential does not allow the anodic dissolution of iron occurring in an actual corrosive reaction to take place, and instead results in the occurrence of abnormal reaction by the accumulation of cations of the electrolyte in the content (for example, Na ions in the case of a 2% NaCl solution) at defective or brittle portions in the inner face of a can of a specimen.

Even when the acceleration potential is more anodic, an anodic difference of less than 50 mV produces small effects in accelerating the corrosive reaction, making it difficult to predict results of a long-term pack test in 48 hours. If the acceleration potential is more anodic by more than 200 mV, chemical reactions which are unlikely to occur in an actual storage environment may take place, such as the aforementioned passivation of the surface at defective or brittle portions in the inner face of a can of a specimen, as well as abnormal gas generation. For example, the electrolysis of water present in a content does not occur in an actual storage environment but does take place when the potential difference between the electrodes is not less than 1.5 V.

Further, an evaluation involving 2% NaCl as the content with the application of a potential difference of about 6 V as adopted in an ERV method results in not only the generation of large amounts of hydrogen gas and oxygen gas associated with water electrolysis but also other phenomena such as the rapid expansion of defective portions due to the generation of chlorine gas and hydrochloric acid at the defects. The ERV methods utilize bubbles generated by these reactions in order to detect exposed metal portions. However, such evaluation tests under conditions inducing these abnormal reactions that do not take place in an actual storage environment cannot be regarded as accelerated evaluation methods for detecting corrosive reactions that occur in a storage environment. The present inventors have carried out anodic polarization measurements with respect to contents composed of various simulated solutions and actual foods containing salts and organic acids. According to the obtained results, the occurrence of the above abnormal reactions may be avoided when the applied potential is not more than 200 mV relative to the immersion potential. Accordingly, it is provided that a constant potential that is more anodic than the immersion potential by 50 mV to 200 mV is applied to cans of specimens.

Example 1

The present invention will be described based on examples.

Half (½) lb cans produced from a laminated steel sheet with a 0.2 mm sheet thickness coated with a copolymerized PET film were degreased with ethanol and were preliminarily evaluated by an ERV method. Thereafter, the cans were washed with water and degreased with ethanol again. Without a retort treatment or a dent treatment, the cans were filled with approximately 170 cc of any of two kinds of contents:

(1) tomato ketchup manufactured by HEINZ (registered trademark) (hereinafter, sometimes referred to simply as "tomato ketchup" or "ketchup"), (2) cut tomato in juice manufactured by AEON (JUSCO) (registered trademark) (hereinafter, sometimes referred to simply as "tomato in juice" or "juice").

These cans were then set in previously provided two measurement apparatuses illustrated in FIG. 1.

Figure 6:
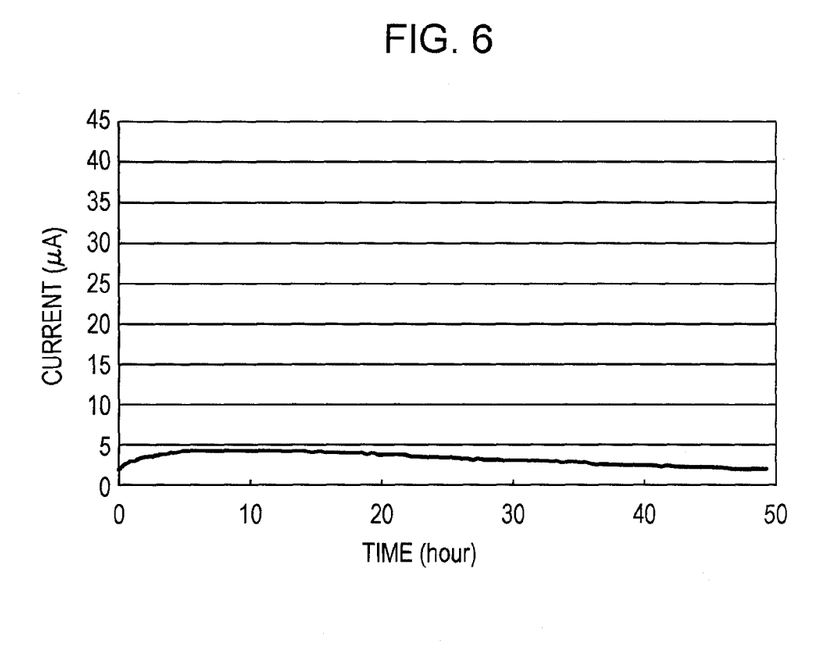
FIG. 6 illustrates an example of measurement with respect to a can filled with tomato in juice.
Figure 7:
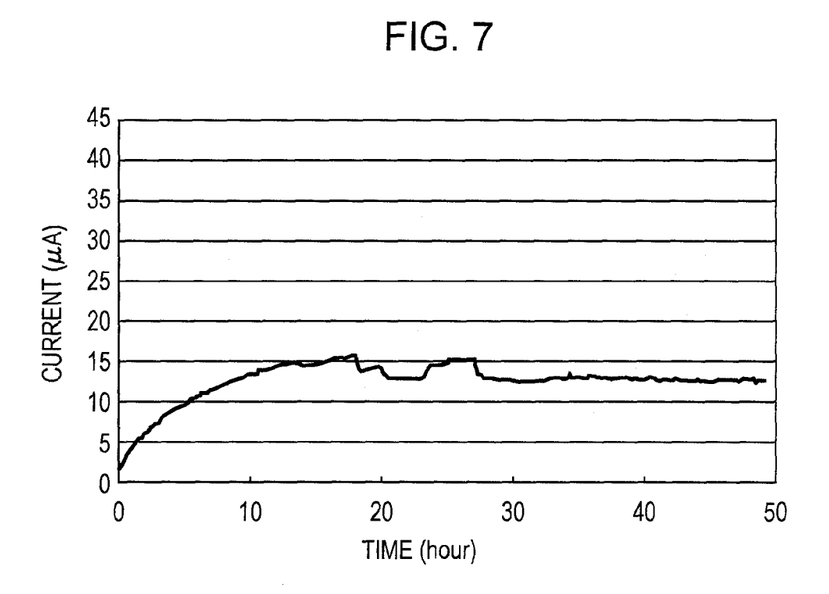
FIG. 7 illustrates an example of measurement with respect to a can filled with tomato ketchup.

First, each of the contents was sealed with an electrolytic cell lid of the measurement apparatus. Thereafter, nitrogen gas was flowed for 30 minutes to saturate (deaerate) the contents, and the ambient temperature was controlled. After the temperature of the contents was confirmed to have been stable at 38° C., the immersion potential was measured. The immersion potentials were −560 mV for the can filled with tomato ketchup and −590 mV for the can filled with tomato in juice. Based on the results, the can filled with tomato ketchup and the can filled with tomato in juice were subjected to the application of potentials that were more anodic than the respective immersion potentials by 100 mV, namely, −460 mV and −490 mV, respectively. In this state, the accumulated amounts of electricity were calculated which had been produced by the anodic current in 48 hours immediately after the initiation of potential application. Similar measurements were further repeated two times using other two ½ lb cans produced from the same laminated steel sheet. Table 1 describes the average values of the accumulated amounts of electricity obtained in the three times of measurements. FIGS. 6 and 7 illustrate examples of the results of measurements in which changes in current passing through the tomato juice-filled can and the tomato ketchup-filled can were measured as a function of time, respectively.

TABLE 1

| | | Tests | |
|---|---|---|---|
| | | Accelerated test (48 hours) | Actual fill test (12 months) |
| | Test methods (test time) Measured item (unit) | Accumulated amount of electricity (C) | Fe concentration (mass ppm) |
| Contents | Tomato ketchup | 1.85 | 107.8 |
| | Tomato in juice | 0.31 | 7.2 |

Table 1 also describes the Fe concentrations obtained by tests in which ½ lb cans produced from the same laminated steel sheet as in the present inventive example were filled with the same contents, closed with lids and seamed, thereafter subjected to a retort treatment in a retort vessel at 120° C. for 30 minutes, and stored at 38° C. for 12 months, followed by opening of the cans and the measurement of Fe concentrations in the contents (tomato ketchup: 107.8 mass ppm, tomato in juice: 7.2 mass ppm). The Fe concentrations were measured by subjecting the whole amount of the content collected from each can to nitric acid decomposition and thereafter to a flameless atomic absorption method. Because the cans stored for 12 months probably had been affected by the retort treatment, the obtained results permitted only an evaluation by the order. However, the order of the accumulated amounts of electricity obtained in the accelerated test is in agreement with the order of the amounts of iron dissolution obtained in the 12 month actual fill test (pack test).

Example 2

Half (½) lb cans produced from a laminated steel sheet with a 0.2 mm sheet thickness coated with a PET-PBT film were evaluated under the same conditions and in the same manner as in EXAMPLE 1. The immersion potentials of the tomato ketchup-filled cans and the tomato juice-filled cans were identical to those in the case of the copolymerized PET cans in EXAMPLE 1. The preliminarily evaluation by an ERV method resulted in 0.1 to 0.4 mA for the copolymerized PET cans in EXAMPLE 1 and 0.1 to 0.5 mA for the PET-PBT cans, and no significant difference was found between the two.

Figure 8:
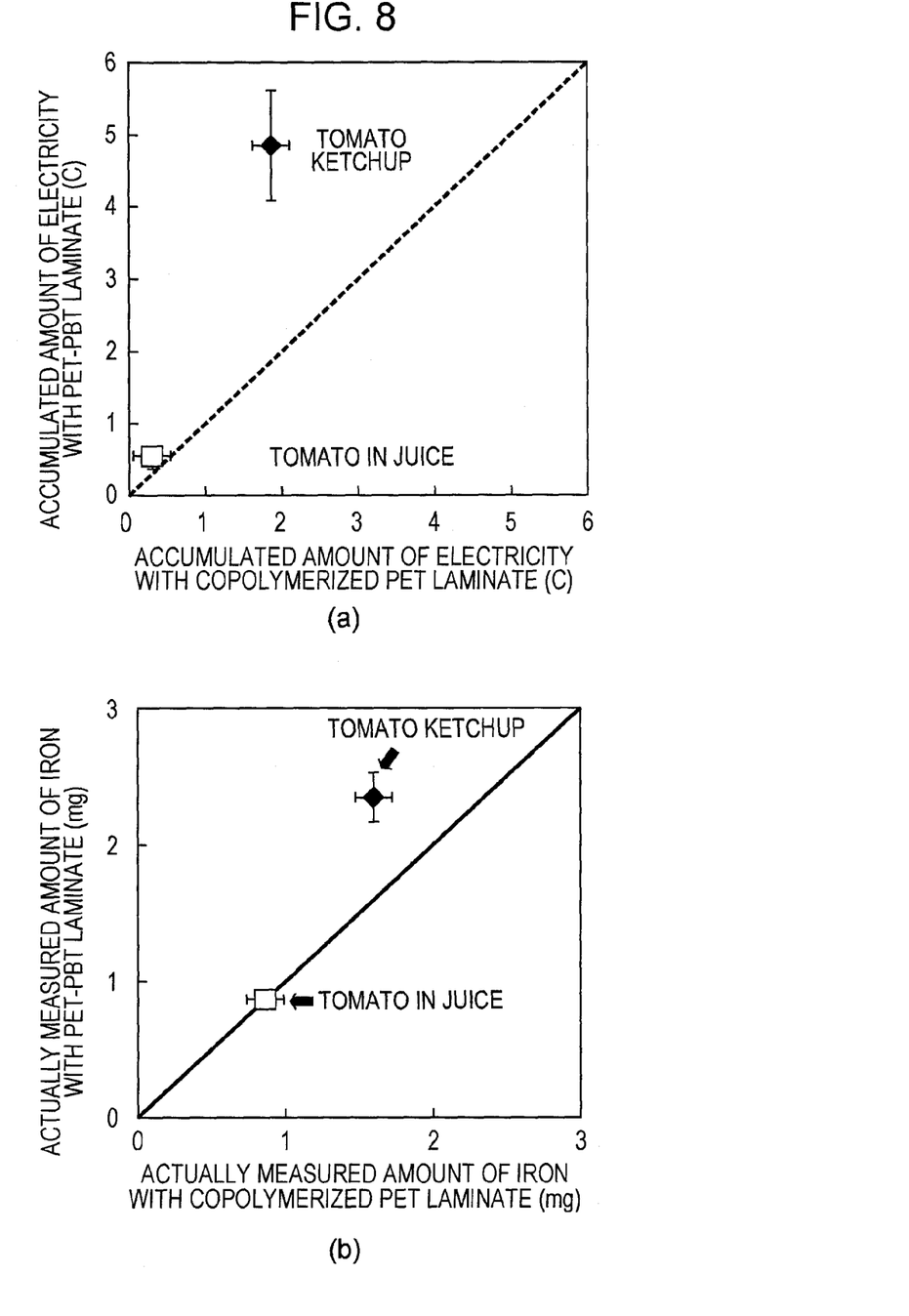
FIG. 8 illustrates a relation (a) between accumulated amounts of electricity and a relation (b) between actually measured amounts of iron, analyzed with respect to PET-PBT cans and copolymerized PET cans filled with tomato in juice and with tomato ketchup.

FIG. 8($a$) shows the accumulated amounts of electricity measured with respect to the PET-PBT cans, plotted against the accumulated amounts of electricity obtained with the copolymerized PET cans in EXAMPLE 1. From the comparison between the PET-PBT cans and the copolymerized PET cans, the PET-PBT can filled with tomato ketchup showed a larger accumulated amount of electricity than that of the copolymerized PET can.

Figure 9:
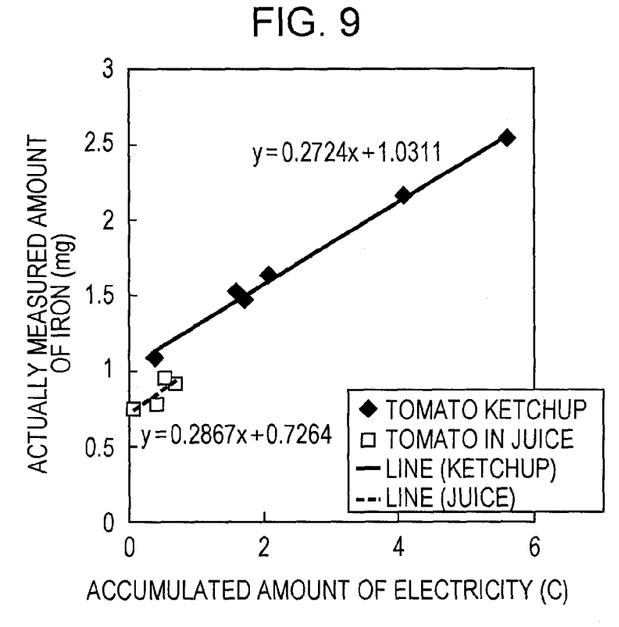
FIG. 9 illustrates relations between an accumulated amount of electricity and an actually measured amount of iron in a content, analyzed with respect to cans filled with tomato in juice and with tomato ketchup.

FIG. 8($b$) illustrates actually measured amounts of iron obtained from the volumes of the contents in the respective cans after the measurements of accumulated amounts of electricity, as well as from their Fe concentrations. FIG. 9 shows the actually measured amounts of iron plotted against the accumulated amounts of electricity. In both cases of the cans filled with tomato in juice and the cans filled with tomato ketchup, the accumulated amounts of electricity and the actually measured amounts of iron have linear relations with an identical slope irrespective of the types of films. As is well known, tomato contains inherent iron. Thus, the values obtained by extrapolating the accumulated amounts of electricity to 0 may be considered as indicating the amounts of inherent iron. That is, the two correlative lines do not overlap with each other because the original amounts of inherent iron are different. When the results are organized with respect to the amounts of dissolved iron, the obtained values are in a proportional relationship with the accumulated amounts of electricity.

Because iron is known to be dissolved in the form of divalent ions, the amount of dissolved iron may be calculated by the following equation provided that all the accumulated amount of electricity is consumed in the dissolution of iron.

$$Q1 = A/55.845 \times 2 \times 96500$$

Here, Q1 is the accumulated amount of electricity (C), A the amount of dissolved iron (g), 55.845 the atomic weight of Fe, 2 the valence of Fe ion, and 96500 the Faraday constant.

Figure 10:
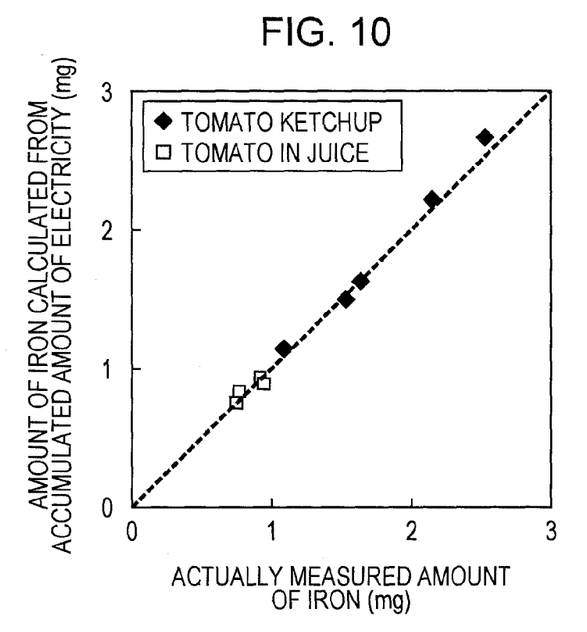
FIG. 10 illustrates a relation between an iron content calculated from the accumulated amount of electricity, and the actually measured amount of iron.

FIG. 10 compares the amounts of dissolved iron calculated in the above manner and combined with the amounts of inherent iron, to the actually measured values. These amounts are shown to be on a single straight line.

These results show that, under conditions within the inventive range such as those described in this example in which an acceleration potential that is more anodic than the immersion potential by 100 mV is applied to specimens filled with contents, only a corrosive reaction (anodic dissolution) occurring by the contact between the contents and defective or brittle portions in the inner face of the specimens is accelerated.

As mentioned above, the accumulated amount of electricity may be considered as a measure of the amount of dissolved iron. Thus, it is possible to predict from the results in FIGS. 8($a$) and ($b$) that the tested copolymerized PET cans are more suitable than the tested PET-PBT cans to contain tomato ketchup as the content, in terms of corrosion resistance in an environment in which cans are stored.

Figure 11:
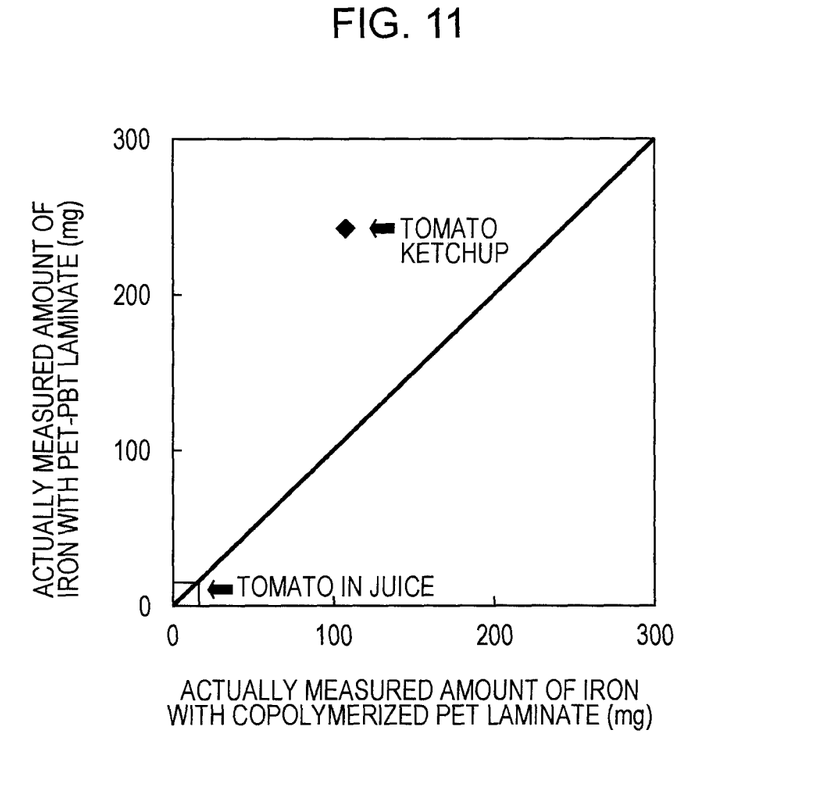
FIG. 11 illustrates a relation (after a 12 month actual fill test) between actually measured amounts of iron analyzed with respect to PET-PBT cans and copolymerized PET cans filled with tomato in juice and with tomato ketchup.

FIG. 11 illustrates the amounts of iron actually measured after a 12 month pack test at 38° C. with respect to similar PET-PBT cans and copolymerized PET cans that had been filled with tomato ketchup and tomato in juice and had been retort treated under the same conditions as in EXAMPLE 1. It is evident from FIG. 11 that the above prediction is correct.

That is, the present invention allows for quick evaluation of the resistance of cans to corrosion by contents without measuring the Fe concentrations in the contents after a long-term pack test.

Example 3

Eighty ½ lb cans coated with a copolymerized PET film were produced and were preliminarily evaluated by an ERV method, thereby selecting 8 cans with values of 0.1 to 0.4 mA (hereinafter, group "a") and 8 cans with values of 0.8 mA or more (hereinafter, group "b"). The ½ lb cans coated with a copolymerized PET film were similar to those used in EXAMPLES 1 and 2. Half of the cans belonging to each group were filled with the tomato ketchup described in EXAMPLES 1 and 2, and the remaining half with the tomato in juice described in EXAMPLES 1 and 2. The thus-prepared specimens, which had a significant difference in the degree of exposure of the base steel sheet caused during the production of cans, were subjected to 4 levels of acceleration potentials, namely, 50, 100, 200 and 300 mV, and the accumulated amounts of electricity were measured for 48 hours and were compared to one another. The results are collectively illustrated in FIG. 12. For each acceleration potential, two curves are shown to indicate the same content. Of such curves, one with a larger accumulated amount of electricity indicates the results of the group "b", and the other with a smaller amount shows the results of the group "a".

Figure 12:
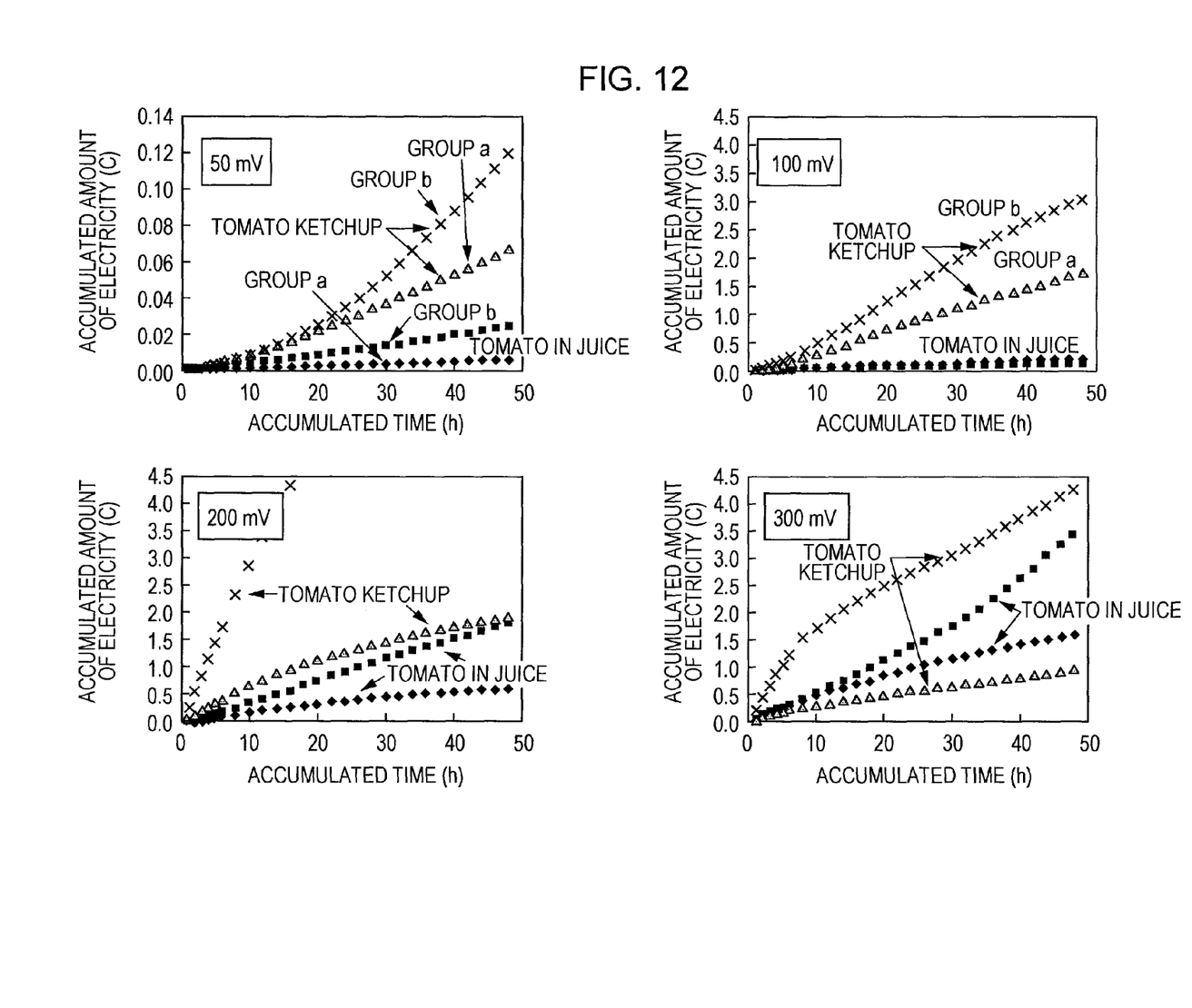
FIG. 12 illustrates a comparison of amounts of electricity accumulated in 48 hours at 4 levels of acceleration potentials (EXAMPLE 3).

At an acceleration potential of 100 mV, larger amounts of electricity were accumulated with strongly corrosive tomato ketchup than with weakly corrosive tomato in juice irrespective of the variations in the degree of exposure of the base steel sheet caused during the production of cans. This order (magnitude relation) caused by contents stood also when the acceleration potential was 50 mV. For each of these acceleration potentials, a clear indication of the order by contents is difficult when the accumulated time is less than 6 hours. At an acceleration potential of 200 mV, the degree of exposure of the base steel sheet caused during the production of cans comes to exert greater influences. Nevertheless, the order by contents narrowly holds good. At an acceleration potential of 300 mV, the order by contents no longer stands and the magnitude relation has become such that it cannot be explained even by the increased influences of the degree of exposure of the base steel sheet caused during the production of cans.

Example 4

Cans were taken arbitrarily from the remaining cans produced in EXAMPLE 3 and were subjected to three times of measurements under conditions involving deaeration (with deaeration) or under conditions involving no deaeration (without deaeration), the measurement conditions except deaeration being the same as in EXAMPLE 1. The results are described in FIG. 13. Amounts of electricity accumulated in 24 hours and those accumulated in 48 hours are shown. As shown, the same tendencies were observed between the two.

Figure 13:
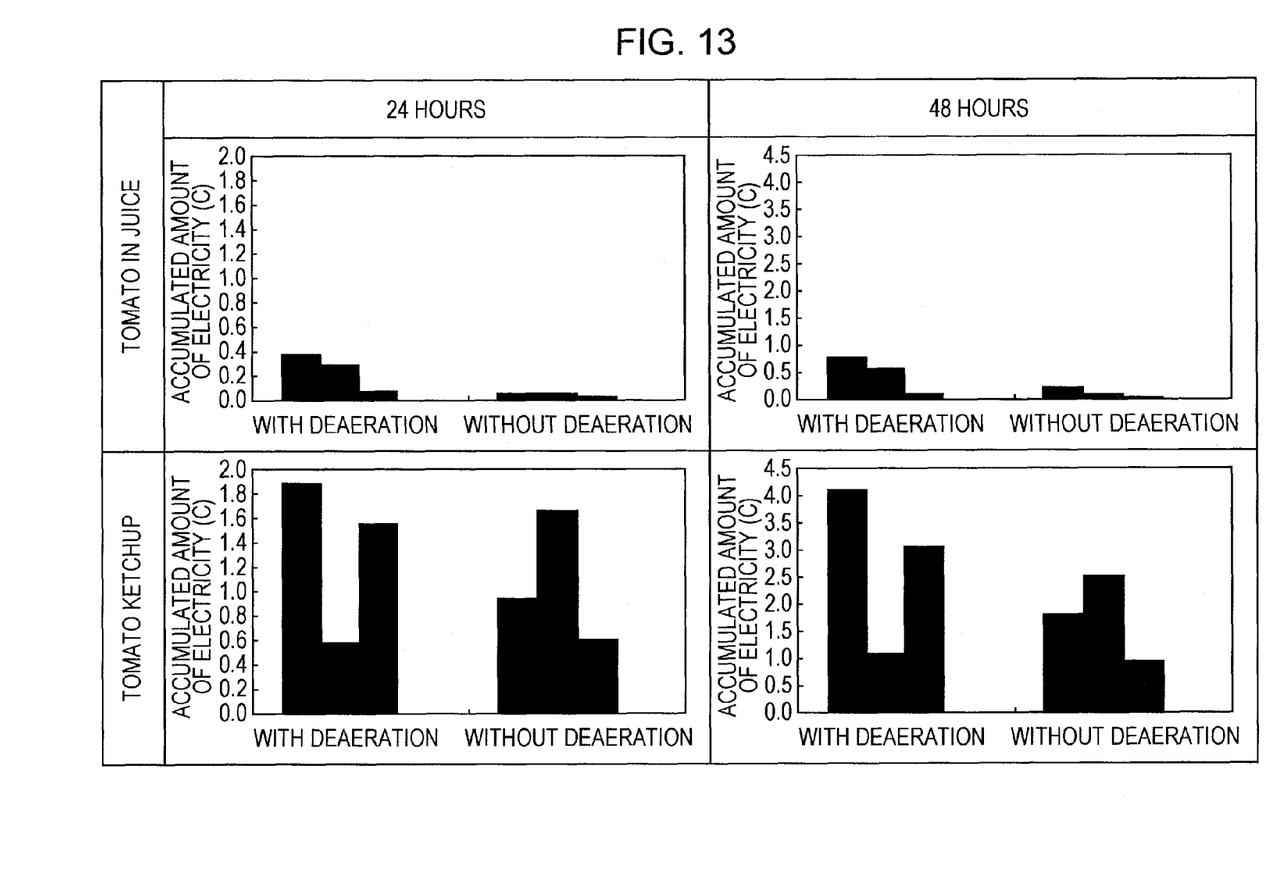
FIG. 13 illustrates a comparison of measurements under conditions involving deaeration (with deaeration) and measurements under conditions involving no deaeration (without deaeration) (EXAMPLE 4).

Under conditions involving no deaeration (without deaeration), there is a probability that the dissolution of iron is also accelerated because the reduction reaction of dissolved oxygen present in the content takes place on the platinum electrode. Thus, it may appear that the accumulated amount of electricity will be larger under conditions involving no deaeration (without deaeration) than under conditions involving deaeration (with deaeration). However, the results in both cases do not show marked differences. This is probably because tomato juice and tomato ketchup have acidic pH of 4.2 and 3.6, respectively, and the hydrogen ions present in large amounts in the contents govern the cathodic reaction on the platinum electrode. Thus, it is at choice whether deaeration is performed or not when evaluating contents which are so acidic that corrosive properties are of particular concern.

Example 5

Results obtained according to the present invention and results obtained by pack tests were compared with respect to 8 kinds in total of commercial contents consisting of the 2 kinds of contents shown in the above examples, namely, tomato juice and tomato ketchup, as well as the following 6 kinds of contents including vegetables, fruits, seafood products and livestock products of which records of 1 year pack tests were available.

- Jalapeno (slices): manufactured by La COSTENA
- Blueberries in syrup: manufactured by MC Beverage
- Black olives: manufactured by BARRA
- Flavored tuna flakes: manufactured by HAGOROMO FOODS CORPORATION
- Sardines in tomato sauce: manufactured by TAWARA CANNING CO., LTD.
- Japanese flavored beef: manufactured by NISSUI The cans used to contain the above contents were the same as the ½ lb cans coated with a copolymerized PET film which had been used in the pack tests.

Because the pack tests had been performed with respect to retort-treated canned products, the present measurement utilized cans which had been packed with water and been subjected to a retort treatment at 120° C. for 30 minutes. The volume of the contents packed into the cans was 120 cc without exception.

The pack tests had involved a thermal filling system called "hot packing" which decreased dissolved oxygen in the contents, and the storage temperature had been 38° C. In view of these facts, the contents were saturated with nitrogen gas to further expel dissolved oxygen present in the contents (deaeration with nitrogen) and the temperature of the contents was controlled at 38° C. The measurements were repeated two times under these conditions with an acceleration potential of 100 mV and an evaluation time of 48 hours.

Figure 14:
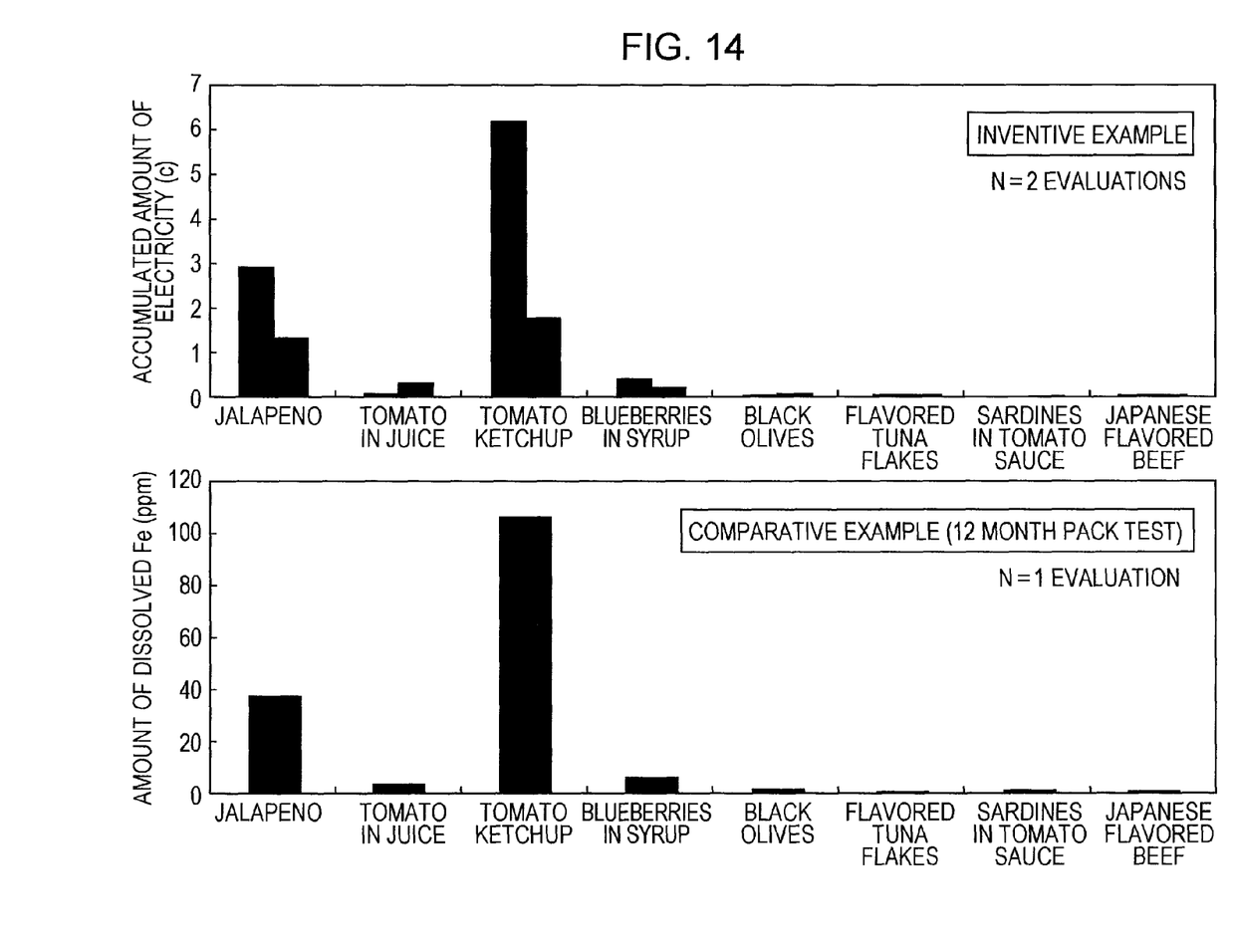
FIG. 14 illustrates a comparison with respect to pack tests with commercially available contents (EXAMPLE 5).

The measurement results are illustrated in FIG. 14 alongside of the results of the pack tests. Two results for each content in the inventive example are derived from the two times of measurements. The results of the pack tests indicate concentrations of dissolved iron in ppm measured after 1 year storage, and these values also are in proportion to the absolute amounts of iron dissolved into the contents similarly to the accumulated amounts of electricity. The results of the two times of measurements in the inventive example show variations which are probably ascribed to the deference in the degree of exposure of the base steel sheet among individual cans. These variations are in good agreement with the order of the results of the pack tests.

REFERENCE SIGNS LIST

1 PLATINUM ELECTRODE CONNECTION OPENING
2 THERMOMETER INSERTION OPENING
3 SALT BRIDGE
4 GAS VENT OPENING
5 NITROGEN GAS INJECTION PIPE
6 SEALING RUBBER PIPE
7 AIRTIGHT STOPPERS (BACKUPS)
8 THERMOMETER
9 SATURATED KCl SOLUTION
10 SPECIMEN (16 FILLED WITH 13)
11 PACKING
12 WATER-SEALED GAS VENT PIPE
13 CONTENT
14 BOTTOM PLATE
15 ELECTRIC WIRE ON SPECIMEN
16 CAN
17 WATER-SEALED BOTTLE
A ELECTROLYTIC CELL LID
B FASTENING MEANS (BOLTS AND NUTS)
C THERMOSTAT MEANS (WATER BATH)
D REFERENCE ELECTRODE (Ag/AgCl ELECTRODE)
E POTENTIOSTAT

The invention claimed is:

1. A method for evaluating the corrosion resistance of a can to a content,
   the can being formed of a metal sheet and having an opening, at least an inner face or both an outer face and an inner face being coated with a resin film or a coating material,
   the method comprising filling the can with the content to form a specimen,
   setting the specimen in an apparatus capable of blocking an outside atmosphere from entering the specimen,
   while maintaining the temperature of the content at a constant temperature in the range of 25 to 60° C., applying a constant potential that is more anodic than an immersion potential by 50 mV to 200 mV to the can of the specimen, and
   evaluating the corrosion resistance of the can to the content based on the accumulated amount of electricity generated during a time appropriately selected from 6 to 48 hours immediately after the application of the constant potential.

2. The method for evaluating the corrosion resistance of the can to the content according to claim 1, wherein the constant anodic potential is applied after the specimen is set in the apparatus capable of blocking an outside atmosphere from entering the specimen and the content is saturated with nitrogen gas to expel dissolved oxygen present in the content.

3. A measurement apparatus for evaluating the corrosion resistance of a can to a content, the apparatus being used in the method for evaluating the corrosion resistance of a can to a content described in claim 1, the apparatus comprising:
   a) an electrolytic cell lid A configured to be tightly compressed against the opening to block an outside atmosphere from entering the specimen, the electrolytic cell lid comprising the following i) to iv):
i) a nitrogen gas injection section,
ii) a gas vent section,
iii) a salt bridge for electrically contacting the content and a reference electrode D disposed outside the specimen through ionic conduction, and
iv) an electrode section for setting a potential difference with respect to the can via the content;

b) a fastening means B for tightly compressing the opening to the electrolytic cell lid A;
c) a thermostat means C for heating and keeping warm the specimen;
d) the reference electrode D; and
e) a potentiostat E connecting the reference electrode D, the electrode section, and the metal sheet forming the can.

4. A measurement apparatus for evaluating the corrosion resistance of a can to a content, the apparatus being used in the method for evaluating the corrosion resistance of a can to a content described in claim 2, the apparatus comprising:

a) an electrolytic cell lid A configured to be tightly compressed against the opening to block an outside atmosphere from entering the specimen, the electrolytic cell lid comprising the following i) to iv):
i) a nitrogen gas injection section,
ii) a gas vent section,
iii) a salt bridge for electrically contacting the content and a reference electrode D disposed outside the specimen through ionic conduction, and
iv) an electrode section for setting a potential difference with respect to the can via the content;

b) a fastening means B for tightly compressing the opening to the electrolytic cell lid A;
c) a thermostat means C for heating and keeping warm the specimen;
d) the reference electrode D; and
e) a potentiostat E connecting the reference electrode D, the electrode section, and the metal sheet forming the can.

\* \* \* \* \*